(12) United States Patent
Kawagishi et al.

(10) Patent No.: US 6,705,996 B2
(45) Date of Patent: Mar. 16, 2004

(54) ULTRASONIC DIAGNOSTIC APPARATUS

(75) Inventors: Tetsuya Kawagishi, Kuroiso (JP); Yoshitaka Mine, Nasu-gun (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/117,081

(22) Filed: Apr. 8, 2002

(65) Prior Publication Data

US 2002/0147398 A1 Oct. 10, 2002

(30) Foreign Application Priority Data

Apr. 9, 2001 (JP) .................................. 2001-110307

(51) Int. Cl.[7] .............................................. A61B 8/14
(52) U.S. Cl. ...................................................... 600/458
(58) Field of Search ................................ 600/437, 440, 600/441, 442–458; 128/916; 341/155; 73/599, 602, 625, 626; 367/7, 11, 130, 138

(56) References Cited

U.S. PATENT DOCUMENTS

| 5,632,277 | A | | 5/1997 | Chapman et al. |
| 5,706,819 | A | | 1/1998 | Hwang et al. |
| 6,440,075 | B1 | * | 8/2002 | Averkiou ................ 600/443 |
| 6,458,084 | B2 | * | 10/2002 | Tsao et al. ................ 600/443 |

* cited by examiner

*Primary Examiner*—Ali M. Imam
(74) *Attorney, Agent, or Firm*—Oblon, Spivak, McClelland, Maier & Neustadt, P.C.

(57) ABSTRACT

An ultrasonic diagnostic apparatus includes an ultrasonic probe, a transmitter for transmitting an ultrasonic wave pulse having peaks at fundamental frequencys, and a receiver for receiving an echo signal corresponding to the ultrasonic wave pulse. The echo signal contains a difference frequency component as well as a fundamental frequency component centered on a fundamental frequency. A difference frequency component is extracted by attenuating the fundamental frequency component of the echo signal. Ultrasonic image data is generated on the basis of the extracted difference frequency component.

29 Claims, 9 Drawing Sheets

FREQUENCY SPECTRUM OF
TRANSMITTED ULTASONIC PULSE
TWO PEAKS

ω1=2MHz (BAND WIDTH: 0.4MHz)
ω2=4MHz (BAND WIDTH: 0.4MHz)

COMBINED ECHO SIGNAL

ADDITION FREQUENCY
COMPONENT (2ω1=4MHz)

COMBINED ECHO SIGNAL

ADDITION FREQUENCY
COMPONENT (2ω1=4MHz)

ULTRASONIC DIAGNOSTIC APPARATUS

CROSS-REFERENCE TO RELATED APPLICATIONS

This application is based upon and claims the benefit of priority from the prior Japanese Patent Application No. 2001-110307, filed Apr. 9, 2001, the entire contents of which are incorporated herein by reference.

BACKGROUND OF THE INVENTION

1. Field of the Invention

The present invention relates to an ultrasonic diagnostic apparatus for visualizing the nonlinear components generated by various nonlinear phenomena in a living body.

2. Description of the Related Art

When an ultrasonic wave propagates through tissues, the waveform is distorted by a nonlinear effect. As a result, a harmonic component is produced. When the ultrasonic wave strikes a microbubble (ultrasonic contrast agent), the microbubble nonlinearly vibrates and collapses. At this time as well, a harmonic component is generated. This mechanism of generating harmonic components is approximately given by a mathematical expression, for example the square of the amplitude of a fundamental frequency component. For this reason, harmonic components are effectively produced in a region with a high sound pressure. As compared with fundamental wave imaging, harmonic imaging has effects of, for example, narrowing transmitted beams and reducing sidelobes. Owing to such effects, images without artifacts can be generated.

In addition, the nonlinearity of an ultrasonic contrast agent is stronger than that of the living tissue. If, therefore, visualization is performed by extracting a harmonic component of a transmitted ultrasonic wave from a received echo, an image with a high contrast between the tissue and the contrast agent can be generated as compared with visualization with a fundamental wave.

A second harmonic is higher in frequency than the fundamental wave (transmitted ultrasonic wave), and hence is greatly influenced by frequency-dependent attenuation. FIG. 1 schematically shows changes in received echo with changes in depth due to the frequency-dependent attenuation in the living body. Referring to FIG. 1, reference numeral 11 denotes the spectrum of a received echo from a shallow region; 13, the spectrum of a received echo from a deep region; and 12, the spectrum of a received echo from an intermediate region. Obviously, with an increase in depth, the spectrum of a received echo shifts to the low frequency side. This phenomenon is a result of the characteristic that attenuation increases with an increase in frequency.

Owing to such a frequency-dependent attenuation characteristic, harmonic imaging has disadvantages, e.g., it is poor in penetration (the greatest depth that can be reached) as compared with fundamental imaging, and it is difficult to realize uniform image quality in the depth direction because the center frequency decreases (azimuth resolution deteriorates) and the band narrows (distance resolution deteriorates) with an increase in depth.

BRIEF SUMMARY OF THE INVENTION

It is an object of the present invention to simultaneously realize narrowing of an ultrasonic beam, a reduction in sidelobe, an improvement in penetration, and uniformity of image quality in the depth direction.

An ultrasonic diagnostic apparatus according to an aspect of the present invention includes an ultrasonic probe, a transmitter for transmitting an ultrasonic wave pulse having peaks at fundamental frequencys, a receiver for receiving an echo signal corresponding the ultrasonic wave pulse, a filter configured to extract a difference frequency component by attenuating a fundamental frequency component centered on a fundamental frequency from the echo signal, and a processor configured to generate ultrasonic image data on the basis of the extracted difference frequency component.

Additional objects and advantages of the present invention will be set forth in the description which follows, and in part will be obvious from the description, or may be learned by practice of the present invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the present invention and, together with the general description given above and the detailed description of the embodiments given below, serve to explain the principles of the present invention.

DETAILED DESCRIPTION OF THE INVENTION

An ultrasonic diagnostic apparatus according to preferred embodiment of the present invention will be described below with reference to the views of the accompanying drawing.

This embodiment has the advantages of conventional harmonic imaging, i.e., "transmitted beam is narrowed" and "sidelobes are reduced", and solves the disadvantages of conventional harmonic imaging, i.e., "it is poor in penetration (the greatest depth that can be reached) as compared with fundamental imaging", and "it is difficult to realize uniform image quality in the depth direction because the center frequency decreases (azimuth resolution deteriorates) and the band narrows (distance resolution deteriorates) with an increase in depth". For this purpose, the embodiment is designed to extract a difference frequency component, instead of an addition frequency component, of the nonlinear components produced by nonlinearity, from an echo signal, and generate an image on the basis of the extracted difference frequency component.

(Arrangement)

Figure 1:
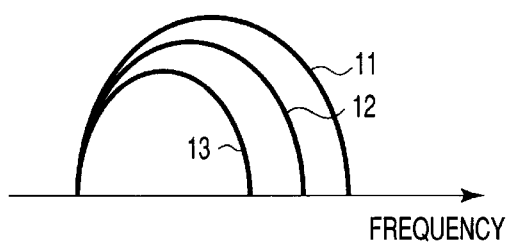
FIG. 1 is a graph showing a frequency-dependent attenuation characteristic of ultrasonic waves with respect to depth.
Figure 2:
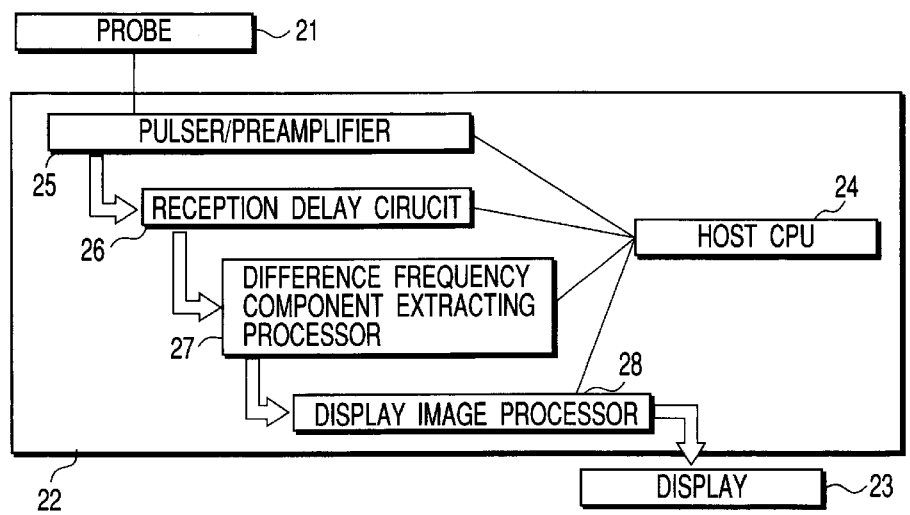
FIG. 2 is a block diagram showing the arrangement of an ultrasonic diagnostic apparatus according to a preferred embodiment of the present invention.

FIG. 2 is a view showing the arrangement of an ultrasonic diagnostic apparatus according to this embodiment. This apparatus is comprised of an apparatus body 22 using a host CPU 24 as a control center, an ultrasonic probe 21 attached to the apparatus body 22, and a display 23 connected to the apparatus body 22. The ultrasonic probe 21 has a plurality of one- or two-dimensionally arranged vibration elements. A pulser/preamplifier (transmitter) 25 having a linear amplifier applies a voltage signal (to be simply referred to as a driving signal hereinafter) that oscillates at a high frequency to each of the plurality of vibration elements. The pulser/preamplifier 25 has a so-called transmission delay control function of shifting the application timings of these driving signals little by little to focus ultrasonic waves at a target depth and provide a deflection angle for an ultrasonic beam. The ultrasonic wave generated by the pulser/preamplifier 25 is one of the most characteristic features of this embodiment, and will be described in detail later.

An ultrasonic wave is transmitted from the ultrasonic probe 21 connected to the apparatus body 22 into the living body, and various nonlinear components are produced by the nonlinearity of the living tissue upon propagation of an ultrasonic wave pulse. A fundamental frequency component and its nonlinear component are back-scattered by an acoustic impedance boundary of the living tissue or a small scatter and received as an echo by the ultrasonic probe 21. A plurality of echo signals generated by a plurality of vibration elements are sent to a reception delay circuit 26 via a receiver including the pulser/preamplifier 25. The reception delay circuit 26 focuses the echoes and performs phased combining of the plurality of echo signals, i.e., received beam forming, to set a reception direction. This apparatus may be equipped with a set of such reception delay circuits 26 to generate a plurality of echo signals in different reception directions from a plurality of echo signals of the same kind, i.e., perform so-called parallel/simultaneous reception. The echo signals are A/D-converted in the reception delay circuit 26, sampled at a sampling frequency suitable for signal processing, and output as digital signals to a processor 27.

The processor 27 extracts a difference frequency component, in particular, from the nonlinear components produced upon nonlinear propagation in the living body. This extraction processing is one of the most characteristic features of this embodiment, and will be described in detail later. The extracted difference frequency component is detected by a display image processor 28 and logarithmically compressed. The resultant data is then output as ultrasonic image data to the display 23 through scan convert processing.

Nonlinear components include addition frequency components and difference frequency components. The addition frequency components include second harmonic components. The difference frequency components include NDC components. This embodiment is characterized in that a difference frequency component is extracted from an echo signal instead of an addition frequency component (conventional harmonic imaging), and the difference frequency component is imaged. In addition, a plurality of techniques associated with difference frequency components will be presented. These extraction techniques will be sequentially described below. The plurality of techniques are preferably installed in the processor 27 to be selectively used by a user.

(First Technique (Visualizing Technique of Difference Frequency Component (NDC Component) Appearing near Zero Frequency)

Figure 3:
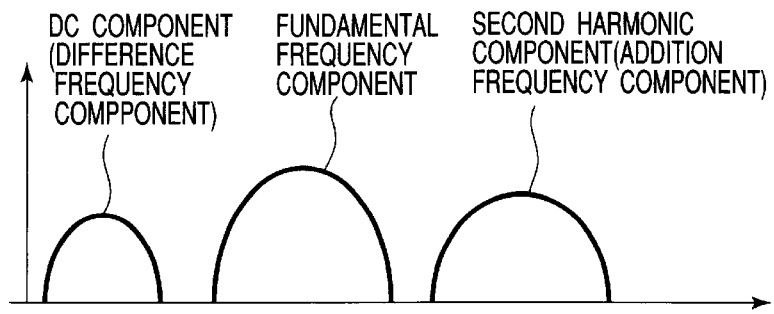
FIG. 3 is a graph showing a fundamental frequency component and nonlinear components (a NDC (Near direct currency) component and second harmonic component) contained in an echo signal in this embodiment.

A difference frequency component appearing near zero frequency, i.e., a "NDC component", is imaged. First of all, nonlinear propagation of tissues can be approximated as the square of a fundamental wave. Letting $\omega$ be the peak frequency of a transmitted ultrasonic wave pulse, i.e., the fundamental frequency, the waveform of an ultrasonic wave pulse to be transmitted is expressed by $a(t)\sin \omega t$. Nonlinear propagation is approximated by $(a(t)\sin \omega t)^2$. It is obvious from this approximate expression that a $2\omega t$ component and NDC component are generated. The former $2\omega t$ component is a so-called addition frequency component, and the latter NDC component is a difference frequency component (see FIG. 3). Conventional harmonic imaging (second harmonic imaging) is a visualizing technique aimed at visualizing an addition frequency component.

In contrast to this, the first technique is a technique of visualizing difference frequency components, in particular, NDC components. Obviously, a NDC component handled by this method does not have a narrow meaning as a zero frequency component but is defined as a frequency component existing in a band with a slight width centered on zero frequency lower than a fundamental frequency f0.

As described above, nonlinear components are mainly produced by nonlinear propagation in tissue and bubble collapse in the contrast agent. To be precise, nonlinearity of propagation is approximated by differentiation of the square of a fundamental wave with time. Therefore, the NDC component produced by squaring substantially does not propagate.

Figure 4:
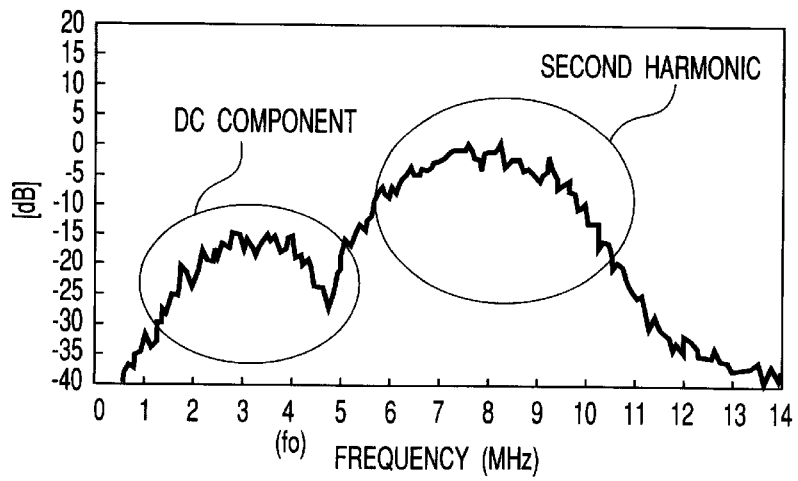
FIG. 4 is a graph showing the frequency spectra of a second harmonic component and NDC component extracted by a so-called phase inversion method of transmitting ultrasonic waves in the same direction at two rates and inverting the phase of a second transmitted ultrasonic wave with respect to the phase of a first transmitted ultrasonic wave.

FIG. 4 shows the frequency spectrum of a nonlinear component extracted by a so-called phase inversion method, in which ultrasonic wave pulses are transmitted to each scan line at two rates, and the phase of an ultrasonic wave pulse at the second rate is inverted with respect to the phase of an ultrasonic wave pulse at the first rate, in a word the phase of an ultrasonic wave pulse at the second rate is shifted at 180° against the phase of an ultrasonic wave pulse at the first rate.

Figure 5A:
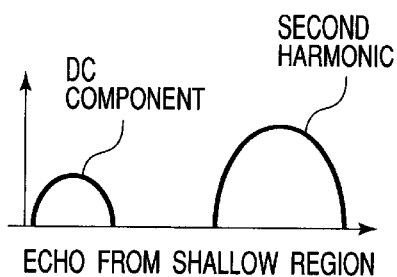
FIG. 5A is a graph showing the frequency spectrum of an echo signal from a relatively shallow region.
Figure 5B:
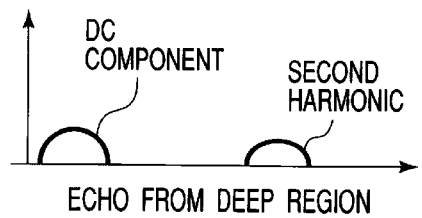
FIG. 5B is a graph showing the frequency spectrum of an echo signal from a relatively deep region.

FIG. 5A shows the frequency spectrum of an echo signal from a relatively shallow region. FIG. 5B shows the frequency spectrum of an echo signal from a relatively deep region. According to frequency-dependent attenuation in a reception path during attenuation in the living body, the attenuation amount of a NDC component with a relatively low frequency is smaller than that of a second harmonic component, as shown in FIG. 4. For this reason, as shown in FIG. 5B, in an echo signal from a relatively deep region at, e.g., 15 cm, the NDC component becomes larger. That is, the NDC component exhibits better penetration than the second harmonic component.

In this case, the harmonic component is a component directly produced from a transmitted ultrasonic wave by the nonlinearity of the living body. Owing to the nonlinearity of a produced harmonic component, various (secondary) harmonic components are produced. However, these components negligibly small.

Figure 6:
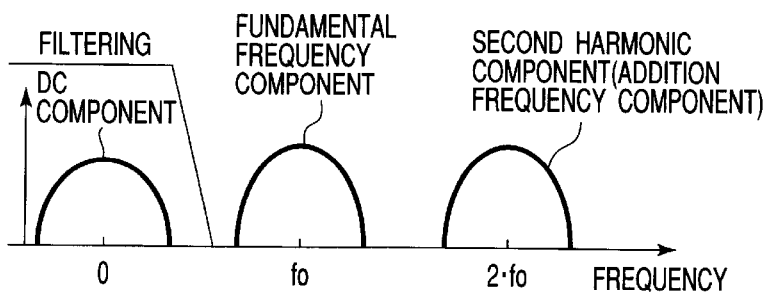
FIG. 6 is a graph for explaining filtering by a difference frequency component extracting processor in this embodiment.

This NDC component is extracted from an echo signal by the processor 27. More specifically, as shown in FIG. 6, the NDC component (difference frequency component) is extracted by low-pass type filtering, i.e., selectively passing only frequency components lower than a near middle frequency (f0/2) between the fundamental frequency f0 and zero frequency and attenuating frequency components higher than f0/2.

Figure 7:
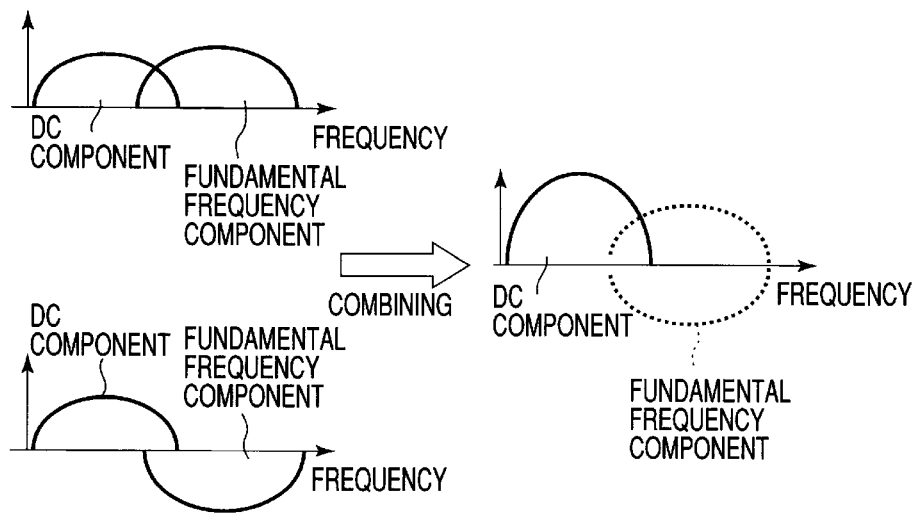
FIG. 7 is a graph showing how the difference frequency component extracting processor combines components obtained at two rates in this embodiment.

A NDC component may be extracted by using the technique (phase inversion method) shown in FIG. 7. Ultrasonic wave pulses having opposite phases are transmitted to each scan line at two rates. With this operation, both a NDC component and fundamental frequency component appear with positive polarity in the echo signal generated by ultrasonic wave pulses at the first rate. In contrast to this, in the echo signal generated by ultrasonic wave pulses at the second rate, a NDC component appears with positive polarity, but a fundamental frequency component appears with negative polarity. This is because the NDC component produced by nonlinear propagation is independent of the polarity of a transmitted ultrasonic wave owing to the principle of its occurrence (square).

By combining the pair of echo signals obtained at the two rates, the fundamental frequency component almost cancels each other out, but the NDC component intensifies. According to this method, even if a fundamental frequency component overlaps a NDC component, only the NDC component can be selectively extracted. In addition, if it is difficult to remove a fundamental frequency component due to the movement of tissue, such difficulty can be eliminated by using a motion compensation technique.

As a matter of course, it is inevitable that an echo signal will be influenced by the frequency characteristics of the reception system (pulser/preamplifier 25 and reception delay circuit 26). For example, the probe 21 typically has a sensitivity band centered on the fundamental frequency f0 and does not cover the entire bands of NDC components in general. Components outside the sensitivity band, i.e. parts of the NDC component contained in an echo signal, components of near zero frequency, are removed by the probe 21.

The pulser/preamplifier 25 generates a driving signal with the highest frequency or a frequency near the highest frequency in the sensitivity band so as to include many NDC components in the sensitivity band of the probe 21. With this operation, an ultrasonic wave has the highest frequency or a frequency near the highest frequency in the sensitivity band of the probe 21 as a fundamental frequency, and the center frequency of NDC components slightly shifts to the high-frequency side relative to zero frequency. This makes it possible to detect most of NDC components using the probe 21. In addition, if a piezoelectric element is made of a single-crystal material having a sensitivity band extended to a frequency near DC, i.e., a relatively broad band characteristic, the probe 21 can detect NDC components more efficiently.

(Second Technique (Transmission of Ultrasonic Wave Having Peaks))

In the first technique described above, an ultrasonic wave having a peak at the single fundamental frequency f0 is transmitted. In this case, a difference frequency component is produced as a NDC component, and an addition frequency component is produced as a second harmonic component.

Figure 8A:
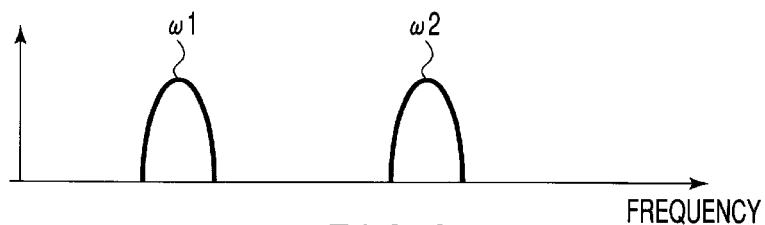
FIG. 8A is a graph showing the frequency spectrum of an ultrasonic wave pulse having a plurality of peaks in this embodiment.
Figure 8B:
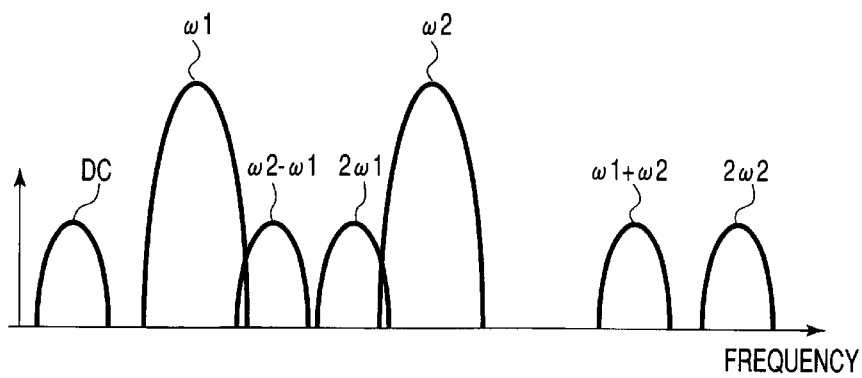
FIG. 8B is a graph showing the frequency spectrum of an ultrasonic echo signal.

In contrast to this, according to the second technique, as shown in FIG. 8A, an ultrasonic wave pulse having peaks (plural) at a plurality of frequencies, two fundamental frequencies ω1 and ω2 (ω1<ω2) in this case, is transmitted. In this case, as shown in FIG. 8B, owing to the nonlinearity (square of a fundamental wave) of living body propagation, a difference frequency component (NDC component, (ω2−ω1) component) and an addition frequency component ((2·ω1) component, (2·ω2), (ω1+ω2)) are produced in accordance with all addition and difference sets of a plurality of peak frequencies.

Note that the two fundamental frequencies ω1 and ω2 are set to satisfy one of the following inequalities:

$$\omega 2 => (\omega 2 - \omega 1) => \omega 1$$

$$\omega 2 => \omega 1 => (\omega 2 - \omega 1)$$

The former inequality is superior to the latter inequality in terms of azimuth resolution. On the other hand, the latter inequality is superior to the former inequality in terms of penetration. The user preferably selects one of the inequalities for every examination in consideration of these superiorities and the examination purpose.

This operation differs from single-peak transmission used in the first technique in that difference frequency components are produced at "ω1−ω2" as well as at a "frequency near DC". The main object of the second technique is to perform visualization in consideration of this. In order to extend the sensitivity band of the probe 21 to a frequency near DC, a special piezoelectric element material or piezoelectric element structure is required. However, most of difference frequency components represented by "ω1−ω2" are included in the sensitivity band of the probe 21 generally used. Therefore, difference frequency components can be efficiently extracted.

As shown in FIG. 8B, a received echo contains fundamental frequency components (ω1, ω2), addition frequency components ((2·ω1), (2·ω2), (ω1+ω2)), and difference frequency components (DC, (ω2−ω1)). In order to extract a desired difference frequency component from an echo signal, the second technique uses both the filter method and the phase inversion method. Although a difference frequency component overlaps a fundamental frequency component on the spectrum, only the difference frequency component can be extracted by removing the fundamental frequency component using the phase inversion method. The phase inversion method can extract all difference frequency components within the reception band, but cannot extract a specific difference frequency component from a plurality of difference frequency components. The filter method is used to extract a specific difference frequency component from a plurality of difference frequency components.

Figure 9:
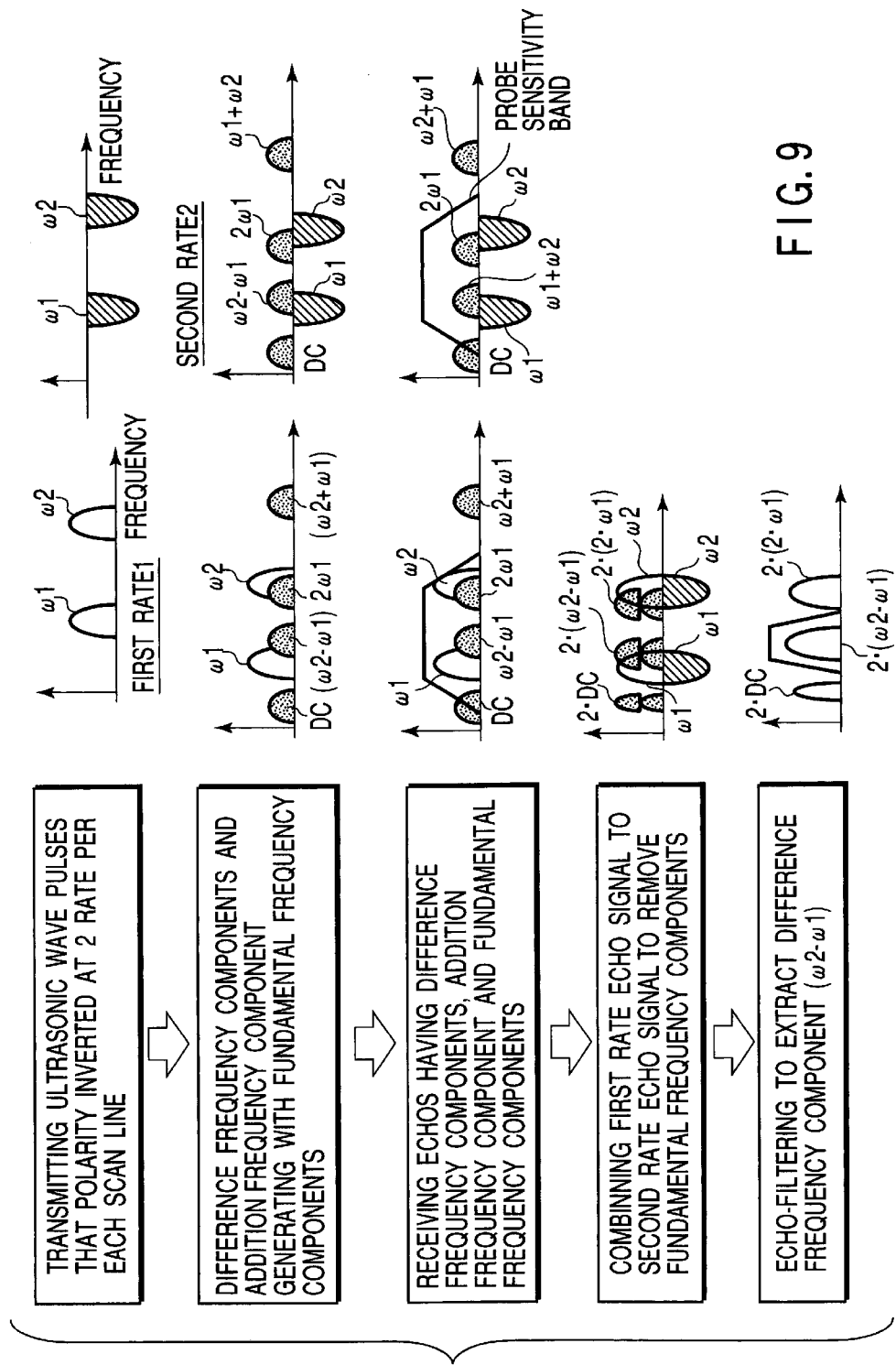
FIG. 9 is a view showing a procedure in the second difference frequency component extraction method in this embodiment.
Figure 10A:
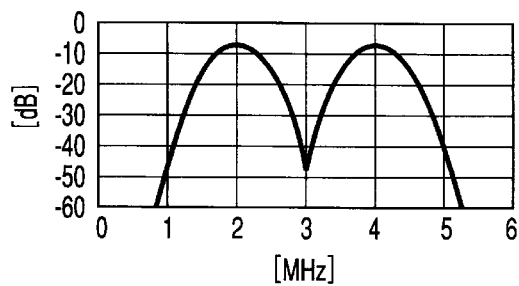
FIGS. 10A and 10B are graphs showing the simulation results on the difference frequency components extracted by the second difference frequency component extraction method in this embodiment.
Figure 10B:
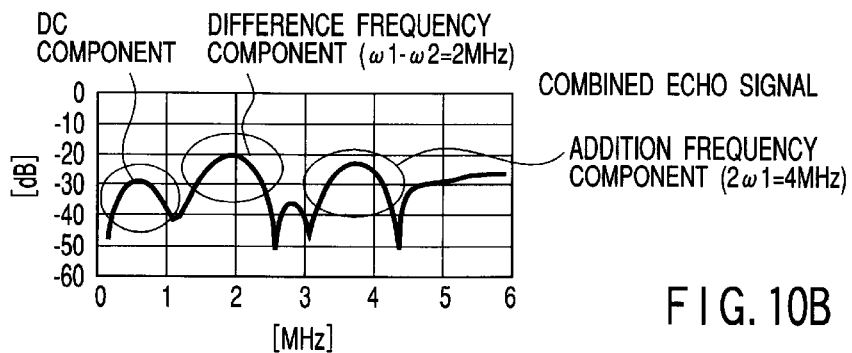

FIG. 9 shows a procedure in the second technique. FIGS. 10A and 10B show the results obtained by simulations of extraction of difference frequency components using the phase inversion method. FIG. 10A shows only the spectrum of a transmitted ultrasonic wave at the first rate (positive polarity transmission). However, ultrasonic wave pulses with inverted polarity, i.e., opposite-phase waveform, are transmitted at the second rate. For nonlinear propagation, an algorithm that applies a difference method to the KZK equation is used. A combined echo signal is obtained by combining received echoes with positive and negative polarities.

With respect to a first (first rate) ultrasonic wave pulse, a second (second rate) ultrasonic wave pulse is transmitted with an opposite phase. The echo at either of the rates contains fundamental frequency components ($\omega 1$, $\omega 2$) and nonlinear components. The nonlinear components include addition frequency components ($2 \cdot \omega 1$, $2 \cdot \omega 2$, $\omega 1 + \omega 2$) and difference frequency components (DC, $\omega 2 - \omega 1$). The fundamental frequency components appear with opposite polarities, whereas the nonlinear components are produced with the same polarity according to the occurrence principle (square).

When such an echo is received by the general probe 21 having a finite sensitivity band, the fundamental frequency components ($\omega 1$, $\omega 2$), part of the difference frequency component near DC, the difference frequency component ($\omega 2 - \omega 1$), and the addition frequency component ($2 \cdot \omega 1$) included in the sensitivity band are converted into electrical signals. However, the remaining part of the difference frequency component near DC and addition frequency components ($2 \cdot \omega 2$, $\omega 1 + \omega 2$) are not converted into electrical signals, and hence are substantially filtered and removed.

To make the most of the filtering effect using the sensitivity band of the probe 21, the fundamental frequency $\omega 2$ is set to the highest frequency or a frequency near the highest frequency in the sensitivity band of the probe 21, and the other fundamental frequency $\omega 1$ is set to the center frequency or a frequency slightly lower than the center frequency in the sensitivity band of the probe 21.

The processor 27 then combines the first-rate echo signal with the second-rate echo signal. As a consequence, the fundamental frequency components appearing with opposite phases cancel each other, and part of the NDC component in the difference frequency components, the difference frequency component ($\omega 2 - \omega 1$), and the addition frequency component ($2 \cdot \omega 1$) theoretically intensify to twice the original intensities. Although the fundamental frequency component $\omega 1$ overlaps the difference frequency component "$\omega 2 - \omega 1$", the fundamental frequency component $\omega 1$ can be removed and the difference frequency component "$\omega 2 - \omega 1$" can be extracted by using the phase inversion method.

In this case, if a specific difference frequency component is "$\omega 2 - \omega 1$", the processor 27 performs band-pass type filtering with respect to a combined signal to pass this difference frequency component and remove other unnecessary difference frequency components, i.e., "NDC component" and "$2 \cdot \omega 1$ component".

With the above processing, only the specific difference frequency component "$\omega 2 - \omega 1$" can be extracted as a component having an intensity twice as high as that of the original component.

This second technique uses the phase inversion method of selectively removing fundamental frequency components and selectively extracting only a nonlinear component. However, a technique of selectively removing fundamental frequency components and selectively extracting only a nonlinear component is not limited to the phase inversion method. For example, the pulse modulation method can be used in place of the phase inversion method.

Figure 11:
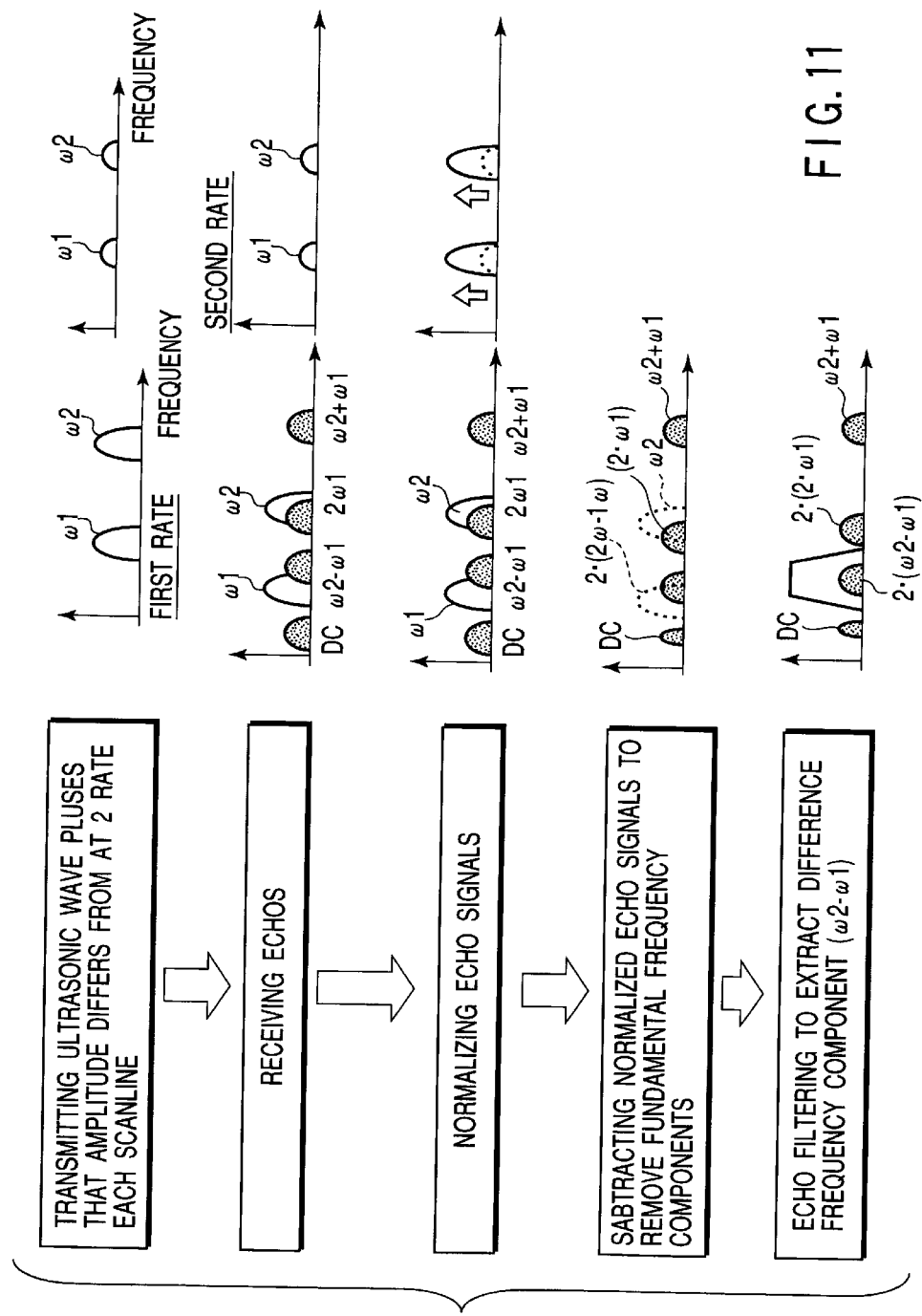
FIG. 11 is a view showing a procedure in a pulse modulation method in this embodiment.

FIG. 11 shows a procedure in the pulse modulation method. As is known, nonlinear components (difference frequency components and harmonic components) are produced in a region exhibiting a high sound pressure, but hardly produced in a region exhibiting a low sound pressure. For example, under the transmission condition of low energy with MI (Mechanical Index) of 0.1 or less, which is obtained by normalizing the maximum peak negative sound pressure on a sound axis with a reference sound pressure of 1 Mpa, fundamental frequency components are produced, but nonlinear components are hardly produced. In contrast to this, under the transmission condition of high energy, nonlinear components are produced as well as fundamental frequency components. The pulse modulation method is a technique for selectively removing fundamental frequency components and selectively extracting only a nonlinear component by using the above characteristics.

In the pulse modulation method, ultrasonic wave pulses are transmitted to each scan line at two rates. As shown in FIG. 11, at the first rate, ultrasonic wave pulses are transmitted at a relatively high amplitude (high sound pressure), e.g., under the transmission condition with MI falling in the range centered at 1.9 or the range of 0.1 exclusive to 0.6 exclusive, more preferably, from 0.3 exclusive to 0.6 exclusive. At the second rate, ultrasonic wave pulses are transmitted at a relatively low amplitude (low sound pressure), e.g., under the transmission condition with MI falling in the range of 0 exclusive to 0.1 exclusive.

At the first rate at which ultrasonic wave pulses are transmitted at a relatively high amplitude, the resultant echo signal contains fundamental frequency components ($\omega 1$, $\omega 2$) and nonlinear components, i.e., the addition frequency components ($2 \cdot \omega 1$, $2 \cdot \omega 2$, $\omega 1 + \omega 2$) and difference frequency components (DC, $\omega 2 - \omega 1$). At the second rate at which ultrasonic wave pulses are transmitted at a relatively low amplitude, the resultant echo signal contains fundamental frequency components with low intensity, but the intensity of nonlinear components in this signal is as low as zero.

The processor 27 normalizes the first- and second-rate echo signals with a transmission sound pressure ratio. For example, the amplitude of the fundamental wave components of the second-rate echo signal is matched with that of the first-rate echo signal by multiplying the second-rate echo signal by the transmission sound pressure ratio between the two rates. The normalized second-rate echo signal contains amplitude-modulated fundamental wave components, but scarcely contains nonlinear components because their intensity is approximately zero.

By subtracting the normalized second-rate echo signal from the first-rate echo signal, therefore, the fundamental frequency components can be removed, and only the nonlinear components are allowed to remain.

Only the target difference frequency component ($\omega 2 - \omega 1$) can be extracted from the remaining nonlinear components by using a filtering function with a pass band centered on ($\omega 2 - \omega 1$)

(Third Technique (Suitable for Visualization of Contrast Agent)

The above first and second techniques can visualize a tissue construction and a microbubble distribution with high image quality. The third technique is suitable for visualization of a contrast agent (microbubbles) which exhibits a nonlinear behavior and for visualization of no tissue construction.

As in conventional harmonic imaging, it is very difficult to discriminate the difference frequency components produced by the nonlinear behavior of a contrast agent from the difference frequency components produced by nonlinear propagation in the tissue. However, by removing the difference frequency components originating from the tissue from the difference frequency components, the difference frequency components originating from the contrast agent alone can be visualized.

Like the second technique, the third technique will be described below in a case where an ultrasonic wave having two frequency peaks is transmitted.

Figure 12:
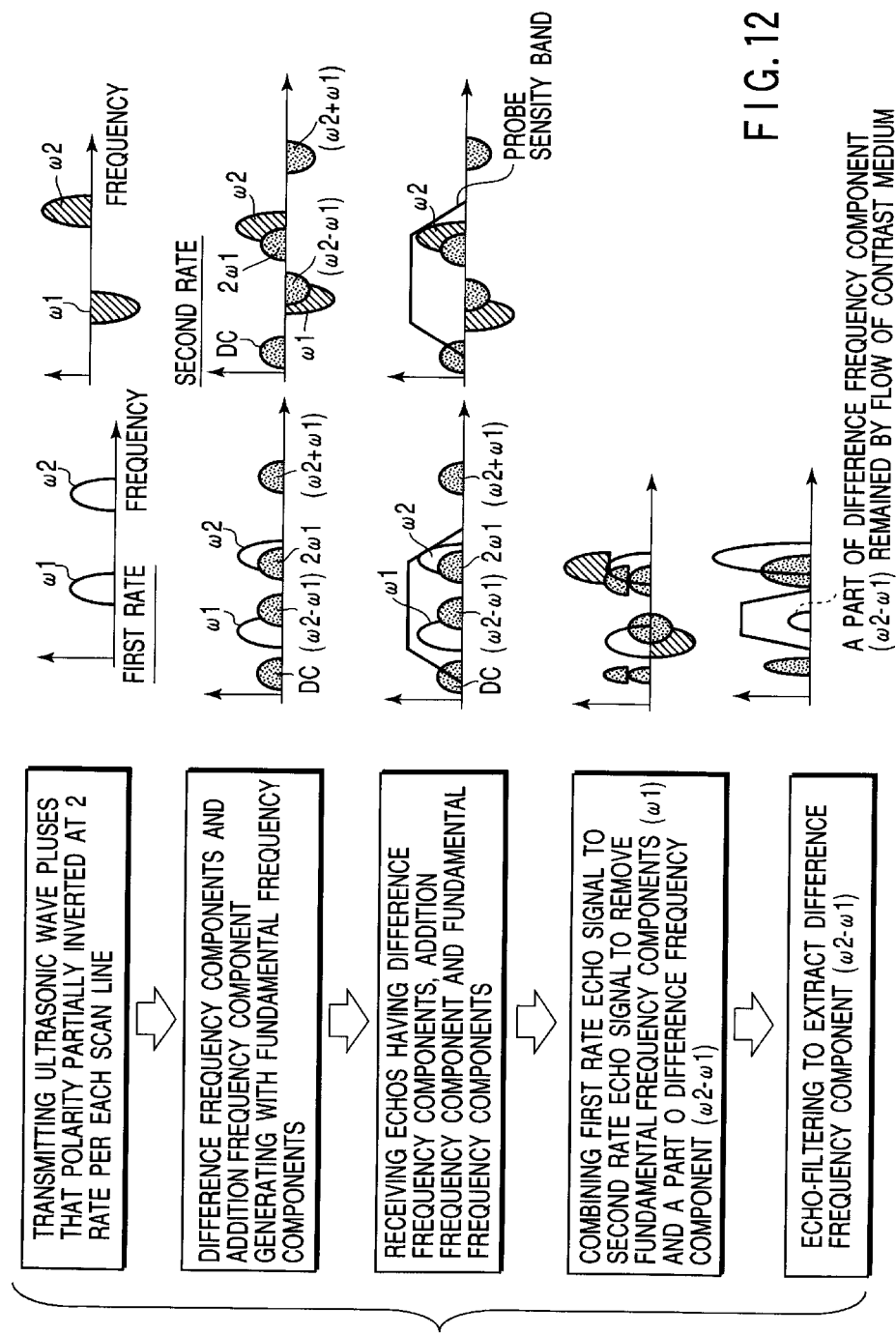
FIG. 12 is a view showing a procedure in the third difference frequency component extraction method in this embodiment.

FIG. 12 shows a procedure in the third technique. According to the second technique, ultrasonic wave pulses having two frequency peaks $\omega 1$ and $\omega 2$ are transmitted at two rates, and the phase of the second-rate ultrasonic wave pulse is inverted with respect to the first-rate ultrasonic wave pulse, i.e., both the two frequency peaks $\omega 1$ and $\omega 2$ are inverted with respect to those of the first-rate ultrasonic wave pulse.

In contrast to this, according to the third technique, ultrasonic wave pulses having the two frequency peaks $\omega 1$ and $\omega 2$ are transmitted at two rates as in the second technique. However, the phase of one frequency peak $\omega 1$ is inverted between the first and second rates, whereas the phase of the other frequency peak $\omega 2$ is not inverted between the first and second rates.

By partially inverting a phase between two rates in this manner, the polarities of the difference frequency component ($\omega 2-\omega 1$) and addition frequency component ($\omega 2+\omega 1$) are inverted between the rates, together with the fundamental frequency component $\omega 1$. However, the polarities of the second harmonic components ($2\cdot\omega 1$, $2\cdot\omega 2$) and NDC component, as well as the fundamental frequency component $\omega 2$, are not inverted between the rates.

The first-rate echo signal is combined with the second-rate echo signal. With this operation, the components (($\omega 2-\omega 1$), ($\omega 2+\omega 1$), and $\omega 1$) whose phases inverted are removed, and the components ($2\cdot\omega 1$, $2\cdot\omega 2$, DC, $\omega 2$) whose phases are not inverted intensify.

In practice, however, the difference frequency component ($\omega 2-\omega 1$) is not completely removed by combining. Even with combining, part of the difference frequency component ($\omega 2-\omega 1$) always remains. Most of the remaining difference frequency component ($\omega 2-\omega 1$) originates from the nonlinear behavior of a contrast agent. The difference frequency component ($\omega 2-\omega 1$) originating from the tissue scarcely remains.

By filtering a combined signal with a pass band centered on ($\omega 2-\omega 1$), the difference frequency component ($\omega 2-\omega 1$) originating from only the contrast agent can be selectively extracted.

Figure 13A:
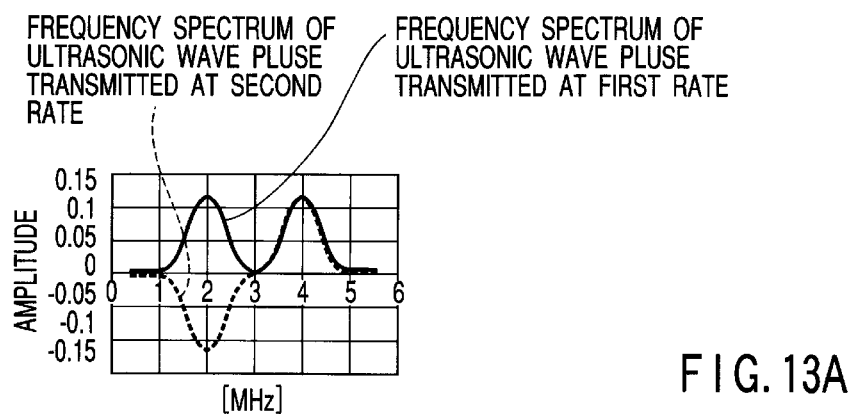
FIGS. 13A and 13B are graphs showing the simulation results on the difference frequency components generated by a nonlinear propagation of tissues, extracted by the third difference frequency component extraction method in this embodiment.
Figure 13B:
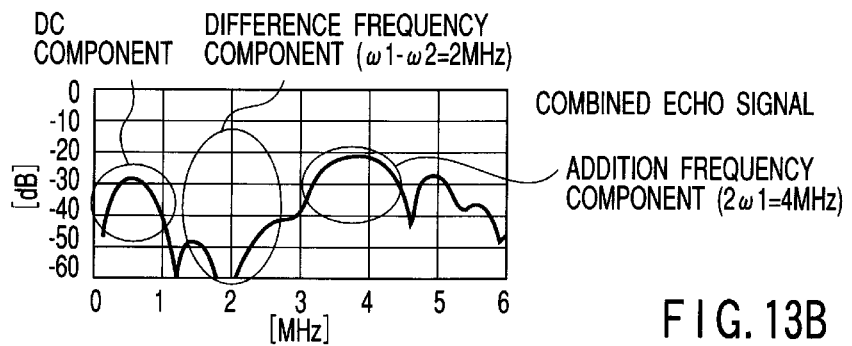

FIGS. 13A and 13B show the simulation results. It is obvious that the difference frequency component produced by nonlinear propagation in the tissue is removed. A technique of correcting movement or the like can also be applied to a case where a difference frequency component is to be visualized.

(Fourth Technique (Suitable for Visualization of Circulatory Organ))

Figure 14:
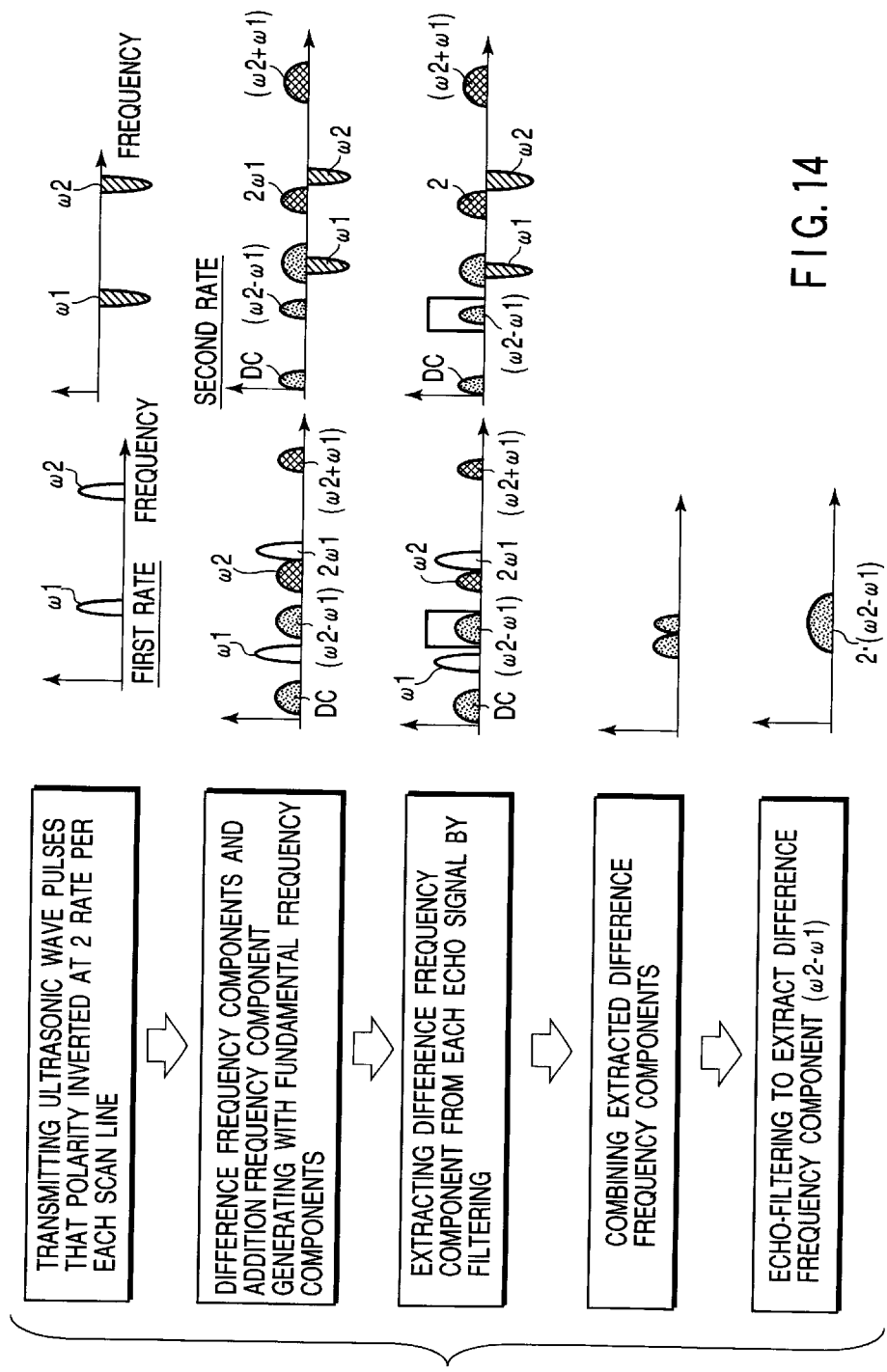
FIG. 14 is a view showing a procedure in the third difference frequency component extraction method in this embodiment.

FIG. 14 shows a procedure in the fourth technique. According to the above second technique, the fundamental frequency components $\omega 1$ and $\omega 2$ are not completely removed by combining, and partially remain. This is because quick movement of a circulatory organ changes the intensity of the fundamental frequency components $\omega 1$ and $\omega 2$ between rates. The remaining fundamental frequency components $\omega 1$ and $\omega 2$ cause motion artifacts on an image. The fourth technique is designed to remove or reduce such motion artifacts.

According to the fourth technique, as shown in FIG. 14, ultrasonic wave pulses having the two frequency peaks $\omega 1$ and $\omega 2$ are transmitted at two rates. The phase of a second-rate ultrasonic wave pulse is inverted with respect to a first-rate ultrasonic wave pulse.

In transmission, to prevent a difference frequency component centered on ($\omega 2-\omega 1$) from overlapping fundamental frequency components centered on $\omega 1$ and $\omega 2$, the frequency spectrum of an ultrasonic wave pulse is narrow-banded around the frequencies $\omega 1$ and $\omega 2$. In addition, the frequencies $\omega 1$ and $\omega 2$ are spaced apart from the difference frequency ($\omega 2-\omega 1$) by a predetermined distance.

Since the difference frequency component ($\omega 2-\omega 1$) does not overlap the fundamental frequency components $\omega 1$ and $\omega 2$, the fundamental frequency components $\omega 1$ and $\omega 2$ can be removed, and the difference frequency component ($\omega 2-\omega 1$) alone can be selectively extracted by performing band pass type filtering with respect to the echo signals at the respective rates with a pass band centered on ($\omega 2-\omega 1$) using the processor 27. The difference frequency component ($\omega 2-\omega 1$) can be almost doubled by combining the first- and second-rate echo signals from which only the difference frequency component ($\omega 2-\omega 1$) is extracted by the filter.

According to the first to third methods, in combining echo signals at the respective rates in phase inversion, if the tissue moves between the rates, a fundamental frequency component remains in some case. In the fourth method, since only a difference frequency component can be selectively extracted by a filter, the influence of a remaining fundamental frequency component due to the movement of the tissue can be eliminated.

Figure 15:
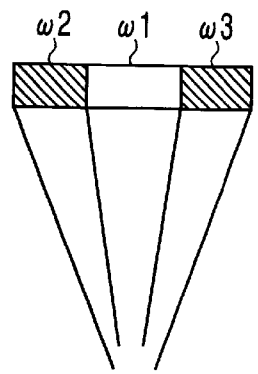
FIG. 15 is a schematic view showing how two peaks are generated from different apertures in this embodiment.

The above description has been made by taking a difference frequency component as an example, and the present invention can be variously modified. All such modifications are included in the gist of the present invention, i.e., control on combined frequency components produced by a nonlinear phenomenon by performing phase control on a fundamental wave (transmission) having a plurality of components and signal processing using a plurality of rates. That is, various combined frequency components (difference frequency components and addition frequency components) can be extracted and removed by performing transmission at a plurality of rates such as phase inversion and control on fundamental frequencies (center frequencies, bands, and phases). A plurality of components need not be realized by a pulser output, and may be transmitted from different apertures, as shown in FIG. 15. In addition, ultrasonic wave pulses may be transmitted under different transmission conditions including a focal point, sound pressure, transmission trigger, aperture, bandwidth and the like.

In addition, the occurrence efficiency of difference frequency components can be controlled by controlling the phase difference between the fundamental frequency component $\omega 1$ and the fundamental frequency component $\omega 2$. If the fundamental frequency $\omega 1$ coincides with the difference frequency (ω2−ω1), so-called degenerated parametric resonance occurs, and the component obtained by combining the fundamental frequency component with the difference frequency component when the above phase difference is 90° intensifies most. An optimal phase relationship may be set in accordance with the purpose of transmission (living body, contrast agent, and curative medicine), and it is important to have a control function in the form of hardware or software.

The above description has been made with attention given to one difference frequency component "ω2−ω1". However, visualization is not limited to only one component, and a plurality of components may be simultaneously visualized. In addition, different components may be visualized at different depths. For example, in a relatively shallow region, a harmonic component as an addition frequency component may be visualized, whereas in a deep region, a difference frequency component exhibiting little attenuation at a low frequency may be visualized. Alternatively, the blend ratio between two components may be continuously changed with changes in depth, or boundaries may be set for blend ratios. Blending can be done either before or after wave detection.

Figure 16A:
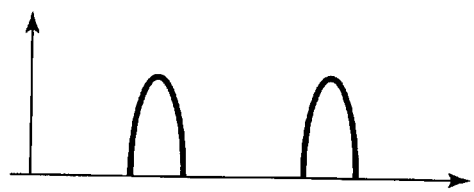
FIGS. 16A and 16B are graphs showing triple-peak transmission in this embodiment.
Figure 16B:
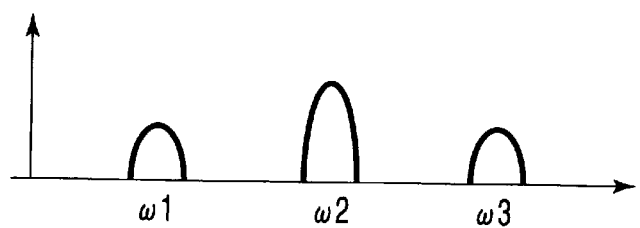

Although the present invention has been described with reference to the transmission of an ultrasonic wave having two peaks as shown in FIG. 16A, in order to generate difference frequency components having the same intensity, an ultrasonic wave having three frequency peaks ω1, ω2, and ω3 may be used, and modulation may be performed such that the two peaks ω1 and ω3 on the two sides of the center peak ω2 are lower in amplitude, as shown in FIG. 16B. In this case, the required making energy is 75% of that required for double-peak transmission. This technique is therefore advantageous in terms of limitations imposed on making energy in terms of heat generation. In order to realize this, it is preferable to use a single-crystal vibration element capable of realizing a broad band.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus comprising:
   an ultrasonic probe;
   a transmitter configured to drive said ultrasonic probe to transmit an ultrasonic wave pulse having a peak at a fundamental frequency;
   a receiver configured to receive an echo signal corresponding to the ultrasonic wave pulse, the echo signal containing a fundamental frequency component centered on the fundamental frequency and a difference frequency component;
   a filter configured to extract the difference frequency component from the echo signal by attenuating the fundamental frequency component; and
   a processor configured to generate ultrasonic image data on the basis of the extracted difference frequency component.

2. An apparatus according to claim 1, wherein said filter configured to extract the difference frequency component selectively passes only a frequency component, of the echo signal, which has a frequency less than a substantially ½ of frequency of the fundamental frequency.

3. An apparatus according to claim 1, wherein the difference frequency component is a component near zero frequency.

4. An ultrasonic diagnostic apparatus comprising:
   an ultrasonic probe;
   a transmitter configured to drive said ultrasonic probe to transmit first and second ultrasonic wave pulses having a peak at a fundamental frequency;
   a receiver configured to receive a first echo signal corresponding to the first ultrasonic wave pulse and a second echo signal corresponding to the second ultrasonic wave pulse, the first and second echo signals respectively containing fundamental frequency components centered on the fundamental frequency and difference frequency components;
   a signal synthesizer configured to synthesize the first and second echo signals to extract the difference frequency components by removing the fundamental frequency components; and
   a processor configured to generate ultrasonic image data on the basis of the extracted difference frequency components.

5. An apparatus according to claim 4, wherein
   the second ultrasonic wave pulse is transmitted with an opposite phase to the first ultrasonic wave pulse, the fundamental frequency component of the second echo signal appears with an opposite polarity to the fundamental frequency component of the first echo signal, and the difference frequency component of the second echo signal appears with the same polarity as that of the difference frequency component of the first echo signal.

6. An apparatus according to claim 4, wherein said transmitter transmits the first and second ultrasonic wave pulses to each scan line at two rates.

7. An apparatus according to claim 4, wherein the difference frequency component is a component near zero frequency.

8. An ultrasonic diagnostic apparatus comprising:
   an ultrasonic probe;
   a transmitter configured to drive said ultrasonic probe to transmit a first ultrasonic wave pulse having peaks at first and second frequencies and transmit a second ultrasonic wave pulse having peaks at the first and second frequencies which is different in a phase from the first ultrasonic wave pulse;
   a receiver configured to receive a first echo signal corresponding to the first ultrasonic wave pulse and a second echo signal corresponding to the second ultrasonic wave pulse, the first and second echo signals respectively containing first fundamental frequency components centered on the first frequency, second fundamental frequency components centered on the second frequency, and difference frequency components between the first and second frequencies;
   a signal adder which adds the first echo signal with the second echo signal, so that the first and second fundamental frequency components of the echo signal being attenuated, and the difference frequency component of the echo signal being remained; and
   a processor configured to generate ultrasonic image data on the basis of the remaining difference frequency component.

9. An apparatus according to claim 8, wherein said transmitter transmits the first and second ultrasonic wave pulses to each scan line at two rates.

10. An apparatus according to claim 8, wherein the first and second frequencies are set to satisfy where ω1 is the first frequency, and ω2 is the second frequency.

11. An apparatus according to claim 8, wherein the first and second frequencies are set in accordance with a user instruction to satisfy where ω1 is the first frequency, and ω2 is the second frequency.

12. An apparatus according to claim 8, wherein said processor has a filtering function for passing a frequency band centered on a difference frequency between the first and second frequencies.

13. An ultrasonic diagnostic apparatus comprising:
an ultrasonic probe;
a transmitter configured to drive said ultrasonic probe to transmit a first ultrasonic wave pulse having peaks at first and second frequencies and transmit a second ultrasonic wave pulse having peaks at the first and second frequencies with an amplitude lower than that of the first ultrasonic wave pulse;
a receiver configured to receive the first echo signal corresponding to the first ultrasonic wave pulse and a second echo signal corresponding to the second ultrasonic wave pulse, the first echo signal containing a first fundamental frequency component centered on the first frequency, a second fundamental frequency component centered on the second frequency, and a difference frequency component between the first and second frequencies, and the second echo signal dominantly containing a first fundamental frequency component centered on the first frequency, and a second fundamental frequency component centered on the second frequency;
a subtractor configured to subtract the normalized first and second echo signals, so that the first and second fundamental frequency components of the echo signal being attenuated, and the difference frequency component of the echo signal being remained; and
a processor configured to generate ultrasonic image data on the basis of the remaining difference frequency component.

14. An apparatus according to claim 13, wherein said transmitter transmits the first and second ultrasonic wave pulses to each scan line at two rates.

15. An apparatus according to claim 13, wherein said processor has a filtering function of passing a frequency band centered on a difference frequency between the first and second frequencies.

16. An ultrasonic diagnostic apparatus comprising:
an ultrasonic probe;
a transmitter configured to drive said ultrasonic probe to transmit first and second ultrasonic wave pulses each having peaks at first and second frequencies, a frequency component of the first frequency of the second ultrasonic wave pulse being set in opposite phase to a frequency component of the first frequency of the first ultrasonic wave pulse, and a frequency component of the second frequency of the second ultrasonic wave pulse being set in phase with a frequency component of the second frequency of the first ultrasonic wave pulse;
a receiver configured to receive a first echo signal corresponding to the first ultrasonic wave pulse and a second echo signal corresponding to the second ultrasonic wave pulse, the first and second echo signals respectively containing first fundamental frequency components centered on the first frequency, second fundamental frequency components centered on the second frequency, and difference frequency components between the first and second frequencies;
an adder configured to add the first and second echo signals, so that the first fundamental frequency components of the echo signal being attenuated, and the difference frequency component of the echo signal being remained; and a processor configured to generate ultrasonic image data on the basis of the remaining component.

17. An apparatus according to claim 16, wherein said transmitter transmits the first and second ultrasonic wave pulses to each scan line at two rates.

18. An apparatus according to claim 16, wherein said processor has a filtering function for passing a frequency band centered on a difference frequency between the first and second frequencies.

19. An ultrasonic diagnostic apparatus comprising:
an ultrasonic probe;
a transmitter configured to drive said ultrasonic probe to transmit a first ultrasonic wave pulse having peaks at first and second frequencies and transmit a second ultrasonic wave pulse having peaks at the first and second frequencies in a phase which is different from the first ultrasonic wave pulse;
a receiver configured to receive a echo signal;
a filter configured to selectively pass frequency component, from the echo signals, in a band centered on a difference frequency between the first and second frequencies; and
a processor configured to generate ultrasonic image data on the basis of the passed frequency component.

20. An apparatus according to claim 19, wherein frequency spectra of the first and second ultrasonic wave pulses are narrow-banded around the first and second frequencies so as to prevent the difference frequency component between the first and second frequencies from overlapping a fundamental frequency component centered on the first frequency.

21. An apparatus according to claim 19, wherein frequency spectra of the first and second ultrasonic wave pulses are narrow-banded around the first and second frequencies so as to prevent the difference frequency component between the first and second frequencies from overlapping a fundamental frequency component centered on the second frequency.

22. An ultrasonic diagnostic apparatus comprising:
an ultrasonic probe;
a transmitter configured to drive said ultrasonic probe to transmit a first ultrasonic wave pulse having a peak at first frequency and a second ultrasonic wave pulse having a peak at second frequency, the first and second ultrasonic wave is transmitted form different position of the ultrasonic probe;
a receiver configured to receive an echo signal;
a filter configured to selectively pass frequency component from the echo signals; and
a processor configured to generate ultrasonic image data on the basis of the filtered frequency component.

23. An apparatus according to claim 19, wherein said transmitter transmits the first and second ultrasonic wave pulses to each scan line at two rates.

24. An ultrasonic diagnostic apparatus comprising:
an ultrasonic probe;
a transmitter configured to drive said ultrasonic probe to transmit ultrasonic wave pulses having peaks at first and second frequencies at a plurality of rates;
a receiver configured to repeatedly receive an echo signal corresponding to the ultrasonic wave pulse;
a signal synthesizer configured to add or subtract the echo signals to extract a difference frequency component; and
a processor configured to generate ultrasonic image data on the basis of the difference frequency component.

25. An method of ultrasonic image generation for ultrasonic diagnostic apparatus comprising:
transmitting an ultrasonic wave pulse having a peak at a fundamental frequency;

receiving an echo signal corresponding to the ultrasonic wave pulse;

extracting a difference frequency component by attenuating the fundamental frequency component from the echo signal; and generating ultrasonic image data on the basis of the extracted difference frequency component.

26. An method of ultrasonic image generation for ultrasonic diagnostic apparatus comprising:

a transmitting first and second ultrasonic wave pulses having a peak at a fundamental frequency;

receiving a first echo signal corresponding to the first ultrasonic wave pulse and a second echo signal corresponding to the second ultrasonic wave pulse;

extracting a difference frequency component by synthesizing the first and second echo signals; and generating ultrasonic image data on the basis of the extracted difference frequency component.

27. An method of ultrasonic image generation for ultrasonic diagnostic apparatus comprising:

a transmitting a first ultrasonic wave pulse having peaks at first and second frequencies and transmit a second ultrasonic wave pulse having peaks at the first and second frequencies;

receiving a first echo signal corresponding to the first ultrasonic wave pulse and a second echo signal corresponding to the second ultrasonic wave pulse;

extracting a difference frequency component by synthesizing the first and second echo signals; and generating ultrasonic image data on the basis of the extracted difference frequency component.

28. An method according to claim 27, wherein said difference frequency component is extracted by a filter.

29. An method of ultrasonic image generation for ultrasonic diagnostic apparatus comprising:

transmitting a first ultrasonic wave pulse having a peak at first frequency from a portion of ultrasonic probe and second ultrasonic wave is transmitted form a other portion of the ultrasonic probe;

receiving a echo signal;

extracting a difference frequency component from the echo signals; and a processor configured to generate ultrasonic image data on the basis of the difference frequency component.

* * * * *